United States Patent [19]

Lidorenko et al.

[11] 4,172,022

[45] Oct. 23, 1979

[54] ELECTROCHEMICAL SENSOR OF HYDROGEN AND HYDROGEN-CONTAINING REDUCING AGENTS

[76] Inventors: Nikolai S. Lidorenko, 3 Mytischinskaya ulitsa, 14 a, kv. 127; Grigory F. Muchnik, ulitsa Preobrazhenskaya, 5/7, kv. 45; Alexandr G. Polyak, Suschevskaya ulitsa, 8/12, kv. 25, all of Moscow; Vasily A. Vakhonin, Toldomsky raion, poselok Zaprudnoe, ulitsa Lenina, 6, kv. 12, Moskovskaya oblast; Vyacheslav M. Krylov, mikroraion Serebryanka, 5, kv. 59, Pushkino Moskovskoi oblasti, all of U.S.S.R.

[21] Appl. No.: 795,708

[22] Filed: May 11, 1977

[51] Int. Cl.² ............................................. G01N 27/46
[52] U.S. Cl. ............................. 204/195 S; 204/195 R; 204/1 T
[58] Field of Search ............... 204/195 R, 1 H, 195 S, 204/1 S; 429/43

[56] References Cited

U.S. PATENT DOCUMENTS

| 3,149,921 | 9/1964 | Warner | 204/1 T |
| 3,410,727 | 11/1968 | Jasinski | 429/43 |
| 3,585,079 | 6/1971 | Richter et al. | 429/43 |
| 3,857,760 | 12/1974 | Breuer et al. | 204/195 S |
| 4,025,412 | 5/1977 | La Conti | 204/195 R |
| 4,049,503 | 9/1977 | Becker et al. | 204/195 R |

FOREIGN PATENT DOCUMENTS

| 2052955 | 5/1972 | Fed. Rep. of Germany | 429/43 |
| 1213364 | 11/1970 | United Kingdom | 429/43 |

*Primary Examiner*—T. Tung
*Attorney, Agent, or Firm*—Lackenbach, Lilling & Siegel

[57] ABSTRACT

The electrochemical sensor of hydrogen and hydrogen-containing reducing agents comprises a cathode which is coal activated with a selective organic catalyst for electrochemical reduction of oxygen, an anode based on the metals of the platinum group and an acidic polymeric electrolyte disposed therebetween. The proposed sensor is capable of operating in a mixture of oxygen with hydrogen or a hydrogen-containing reducing agent without separation of the components. The sensitivity of the sensor to hydrogen is $10^{-3}$ to $10^{-4}$ percent by volume.

7 Claims, 1 Drawing Figure

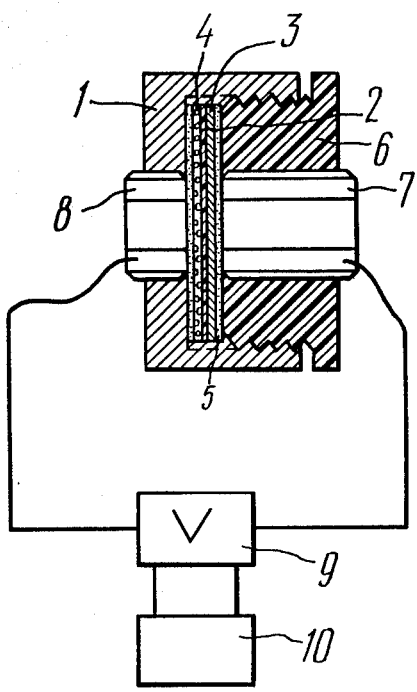

ELECTROCHEMICAL SENSOR OF HYDROGEN AND HYDROGEN-CONTAINING REDUCING AGENTS

The present invention relates to chemotronics, and more particularly to an electrochemical sensor of hydrogen and hydrogen-containing reducing agents.

The invention is applied in shops and premises wherein an explosion hazard associated with hydrogen and hydrogen-containing reducing agents exists, as well as for controlling installations and different systems working with hydrogen or hydrogen-containing reducing agents directly in the process of operation, for controlling the tightness of welded joints, welds and various other joints where the indicator gas used is hydrogen or a hydrogen-nitrogen mixture, and also for detecting the presence of hydrogen in inert gases.

At present, the principal instruments for detecting the presence of hydrogen in air are those which are based on the principle of the resistance thermometer whose sensitive element is a platinum filament. A precise current value is passed through the platinum filament by means of a special stabilizer. When the air-hydrogen mixture gets onto the filament, catalytic combustion of hydrogen takes place accompanied by a change in the filament resistance, and correspondingly, a voltage drop which is registered by a bridge circuit.

Such an arrangement for detecting hydrogen in air is rather complicated which lowers its reliability. Known in the art is U.S. Pat. No. 3,149,921 to Warner which discloses an electrochemical device for detecting hydrogen comprising an anode, a cathode and an electrolyte disposed therebetween. The anode and the cathode are activated by the same catalyst—platinum black. Obviously, insulation of the cathode from the environment and supply to the cathode of pure oxygen or air which does not contain reducing components, are required for operation of this sensor in the air-hydrogen mixture or a corresponding reducing agent. This involves the complexity of the design and considerably lowers the reliability of the entire system on the whole, particularly in long operation.

It is an object of the present invention to simplify the design and improve the reliability of operation of the system.

It is another object of the invention to provide an electrochemical sensor operating on the principle of a current source in a mixture of oxygen of the air and hydrogen or a respective hydrogen-containing reducing agent directly without separating the components.

In accordance with the above-mentioned and other objects the invention substantially resides in the proposed electrochemical sensor of hydrogen and hydrogen-containing reducing agents comprising a cathode, an anode based on the metals of the platinum group and an acidic polymeric electrolyte disposed therebetween. According to the invention, the cathode is coal activated with a selective organic catalyst for electrochemical reduction of oxygen.

The use of said catalyst makes it possible for the sensor to operate as a current source in a mixture of oxygen, hydrogen or hydrogen-containing reducing agents directly without preliminary separation of the components.

For operation of the sensor in inert gases it is recommended, according to the invention, to use chloroquinones as well as redox polymers as a selective organic catalyst for electrochemical reduction of oxygen.

It is advisable, according to the invention, to use polymer or monomer phthalocyanines of transition metals as the organic catalysts.

It is preferable, according to the invention, to use tetrachloroparabenzoquinone, a copolymer of formaldehyde and pyrocatechol, and polymer and monomeric iron phthalocyanine as the organic catalyst.

Other objects and advantages of the present invention will be understood from the following detailed description and the accompanying drawing which shows the circuit diagram of the sensor.

The herein-proposed electrochemical sensor of hydrogen and hydrogen-containing reducing agents comprises a housing 1 (FIG. 1) wherein an acidic polymeric electrolyte 2 is disposed in the form of a membrane. On one side of the electrolyte 2 there is disposed an anode 3 which is represented by platinum black or a grid. On the other side of the membrane there is disposed a cathode 4 which is represented by coal activated with a selective organic catalyst for electrochemical reduction of oxygen. Used as such catalysts are chloroquinones, redox polymers, monomeric and polymeric phthalocyanines of transition metals. The catalysts are deposited on coal powder by precipitation from respective solutions.

The anode 3 and the cathode 4 are pressed against the electrolyte 2 with porous graphite current collectors 5. The whole assembly is secured by means of a nut 6. The current is led off through metal contacts 7 and 8 with a soldered wire, said contacts being connected to the input of a pre-amplifier 9 whose output is connected to a sound, light or digital indicator 10.

The proposed sensor operates preferably in the following manner.

When hydrogen gets into the atmosphere it is adsorbed on the surface of the platinum anode 3 according to the equation:

$$H_2 \rightarrow 2H \text{ adsorbed} \quad (1)$$

$$H \text{ ads}, -e \rightarrow H^+ \quad (2)$$

The electrons formed as a result of this reaction pass along the external circuit to the cathode 4 activated, for example, by tetrachloroparabenzoquinone where the following reaction takes place:

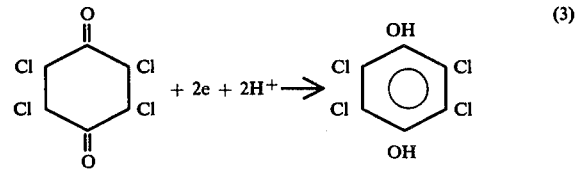

Oxygen which is in the atmosphere reacts with the hydroquinone formed according to the following formula

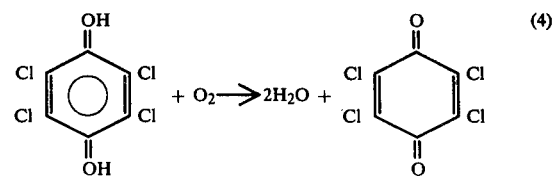

The summary current-forming reaction:

$$\underset{\underset{O}{\overset{O}{\underset{\|}{\overset{\|}{\bigcirc}}}}}{\overset{2e\downarrow}{\underset{Cl}{\overset{Cl}{\text{Cl}}}\underset{Cl}{\overset{Cl}{\text{Cl}}}}} + H_2 \longrightarrow \underset{\underset{OH}{\overset{OH}{\underset{|}{\overset{|}{\bigcirc}}}}}{\underset{Cl}{\overset{Cl}{\text{Cl}}}\underset{Cl}{\overset{Cl}{\text{Cl}}}} \quad (5)$$

Thus, when hydrogen gets onto platinum the sensor starts generating electric current whose value is proportional to the concentration of hydrogen. This current is amplified with the pre-amplifier 9 which energizes the indicator 10.

The advantage of the invention is that the proposed sensor being essentially a fuel element, is capable of operating in a mixture of oxygen of the air and hydrogen or a hydrogen-containing reducing agent without separating the components.

The sensor 7 is characterized by high reliability, a low internal resistance (not more than 50 ohm), a simple design, small size, and is easy to make.

In addition, owing to using an acidic polymeric electrolyte the sensor is not sensitive to carbonization.

The sensitivity to hydrogen and hydrogen-containing reducing agents is $10^{-3}$ to $10^{-4}$ percent by volume.

The sensor can be used for detecting hydrazine, formaldehyde, propane and other substances shifting the potential of the platinum electrode to the negative side.

For a better understanding of the present invention specific examples are presented below.

EXAMPLE 1

The electrochemical sensor of hydrogen with a cathode 4 activated with tetrachloroparabenzoquinone (a mixture with coal with a ratio of 1:1) and an anode 3 activated with platinum black (the amount of the catalyst corresponds to 10 mg/cm$^2$) is connected to a resistance R=100 ohm. By means of a high-resistance cathode voltmeter the voltage drop is measured across this resistance. The sensor with the resistance is placed in an air-tight glass cell and the high-resistance cathode voltmeter is connected through air-tight leads. When there is no hydrogen the voltage drop across the resistance is zero. Then a mixture of air with hydrogen with an amount of hydrogen of $10^{-3}$ percent by volume is blown through the air-tight cell. The hydrogen content in the air being blown through is controlled with a chromatograph. When said mixture of air and hydrogen is being blown through the cell the voltage drop across the resistance measured through the cell by the cathode voltmeter is $70 \cdot 10^{-6}$ V.

EXAMPLE 2

In the electrochemical sensor the cathode 4 is activated with monomeric iron phthalocyanine (a mixture with coal with a ratio of 1:1). The sensor is used for detecting hydrogen in a manner similar to Example 1.

The voltage drop across the resistance is $50 \cdot 10^{-6}$ V.

EXAMPLE 3

The electrochemical sensor with the cathode 4 activated with polymeric iron phthalocyanine (a mixture with coal with a ratio of 1:1) is used for detecting hydrogen in a manner similar to Example 1.

The voltage drop across the resistance is $50 \cdot 10^{-6}$ V.

EXAMPLE 4

The electrochemical sensor of hydrogen with the cathode activated with polymeric cobalt phthalocyanine (a mixture with coal with a ratio of 1:1) is tested in a manner similar to the sensor in Example 1. The voltage drop is $50 \cdot 10^{-6}$ V.

EXAMPLE 5

The electrochemical sensor of hydrogen with the cathode activated with orthotetrachlorobenzoquinone (a mixture with coal with a ratio of 1:1) is tested in a manner similar to Example 1. The voltage drop is $50 \cdot 10^{-6}$ V.

EXAMPLE 6

The electrochemical sensor of hydrogen with the cathode activated with a redox polymer, namely a copolymer of formaldehyde and pyrocatechol, in a mixture with coal (with a ratio of 1:1) is tested in a manner similar to Example 1. The voltage drop is $50 \cdot 10^{-6}$ V.

EXAMPLE 7

The electrochemical sensor as in Example 1 is tested in a mixture of air and propane with a concentration of propane of $10^{-2}$ percent by volume. The propane concentration is measured by a chromatograph.

The voltage drop across the resistance is $30 \cdot 10^{-6}$ V.

EXAMPLE 8

The electrochemical sensor as in Example 2 is tested in a mixture of air and vapors of formaldehyde, the latter having a concentration of $10^{-2}$ percent by volume. The concentration of formaldehyde is measured by a chromatograph.

The voltage drop across the resistance is $30 \cdot 10^{-6}$ V.

EXAMPLE 9

The electrochemical sensor, as in Example 3, is tested in a mixture of air with hydrazine, the latter having a concentration of $10^{-2}$ percent by volume.

The voltage drop across the resistance is $30 \cdot 10^{-6}$ V.

EXAMPLE 10

The electrochemical sensor with the cathode 4 activated with a copolymer of orthotetrachlorobenzoquinone and benzidine, in a mixture with coal (a ratio of 1:1), is tested in a mixture of air and hydrogen in a manner similar to Example 1.

The voltage drop across the resistance is $50 \cdot 10^{-6}$ V.

What is claimed is:

1. An electrochemical sensor of hydrogen and hydrogen-containing reducing agents adapted to operate as a current source in a mixture of oxygen, hydrogen or hydrogen-containing reducing agents directly without preliminary separation of the components comprising:
    a cathode of coal powder in contact with a selective organic catalyst from the group consisting of chloroquinones, redox polymers; and polymer or monomer phthalocyanines of a transition metal;
    a platinum anode; and
    an acidic polymeric electrolyte disposed between the cathode and the anode.

2. An electrochemical sensor according to claim 1, wherein said catalyst is tetrachloroparabenzoquinone.

3. An electrochemical sensor according to claim 1 wherein said catalyst is a copolymer of formaldehyde and pyrocatechol.

4. An electrochemical sensor according to claim 1 wherein said catalyst is a phthalocyanine polymer of a transition metal.

5. An electrochemical sensor according to claim 4 wherein said catalyst is polymeric iron phthalocyanine.

6. An electrochemical sensor according to claim 1 wherein said catalyst is monomeric phthalocyanines of a transition metal.

7. An electrochemical sensor according to claim 6 wherein said catalyst is monomeric iron phthalocyanine.

* * * * *